United States Patent
Osumi

(10) Patent No.: US 10,695,031 B2
(45) Date of Patent: Jun. 30, 2020

(54) ULTRASONIC DIAGNOSTIC APPARATUS, IMAGE PROCESSING APPARATUS, AND IMAGE PROCESSING METHOD

(71) Applicant: TOSHIBA MEDICAL SYSTEMS CORPORATION, Otawara-Shi (JP)

(72) Inventor: Ryota Osumi, Nasushiobara (JP)

(73) Assignee: CANON MEDICAL SYSTEMS CORPORATION, Otawara-shi (JP)

( * ) Notice: Subject to any disclaimer, the term of this patent is extended or adjusted under 35 U.S.C. 154(b) by 583 days.

(21) Appl. No.: 14/596,519

(22) Filed: Jan. 14, 2015

(65) Prior Publication Data

US 2015/0126867 A1    May 7, 2015

Related U.S. Application Data

(63) Continuation of application No. PCT/JP2013/074288, filed on Sep. 9, 2013.

(30) Foreign Application Priority Data

Sep. 10, 2012 (JP) ................................. 2012-198754
Sep. 9, 2013 (JP) ................................. 2013-186540

(51) Int. Cl.
A61B 8/08    (2006.01)
A61B 8/06    (2006.01)
A61B 8/14    (2006.01)

(52) U.S. Cl.
CPC .............. *A61B 8/485* (2013.01); *A61B 8/06* (2013.01); *A61B 8/08* (2013.01); *A61B 8/14* (2013.01); *A61B 8/488* (2013.01); *A61B 8/5223* (2013.01)

(58) Field of Classification Search
None
See application file for complete search history.

(56) References Cited

U.S. PATENT DOCUMENTS

2007/0100237 A1    5/2007    Okamura et al.
2008/0071174 A1*   3/2008    Waki .................. A61B 8/08
                                                          600/442

(Continued)

FOREIGN PATENT DOCUMENTS

CN          1980606 A     6/2007
CN        101044989 A    10/2007

(Continued)

OTHER PUBLICATIONS

Ophir et al., "Review Article: Elastography: Imaging the Elastic Properties of Soft Tissues with Ultrasound". J. Med. Ultrasonics 2002; 29, pp. 155-171.*

(Continued)

*Primary Examiner* — Katherine L Fernandez
*Assistant Examiner* — Yi-Shan Yang
(74) *Attorney, Agent, or Firm* — Oblon, McClelland, Maier & Neustadt, L.L.P.

(57) ABSTRACT

An ultrasonic diagnostic apparatus according to an embodiment includes a signal processing unit, an indicator calculating unit, a storage unit and a controller. The signal processing unit generates, based on a reflection wave signal of an ultrasonic wave that is transmitted into a subject, strain information about a strain of a tissue that is pressured and released in the subject in chronological order. The indicator calculating unit calculates an indicator of a state of pressure and release to the tissue at generation of the strain information. The storage unit stores a time phase at generation of the strain information and the indicator at generation of the strain information in an associated manner. The controller extracts a candidate time phase being a time phase of a candidate based on the indicator associated with each of the time phase.

16 Claims, 9 Drawing Sheets

(56) References Cited

U.S. PATENT DOCUMENTS

| | | | |
|---|---|---|---|
| 2008/0196506 A1 | 8/2008 | Satoh et al. | |
| 2008/0269605 A1 | 10/2008 | Nakaya | |
| 2008/0269606 A1* | 10/2008 | Matsumura | A61B 5/0048 |
| | | | 600/438 |
| 2009/0203997 A1* | 8/2009 | Ustuner | A61B 8/08 |
| | | | 600/443 |
| 2010/0041994 A1* | 2/2010 | Abe | A61B 8/429 |
| | | | 600/443 |
| 2012/0321165 A1 | 12/2012 | Suda | |
| 2015/0141822 A1* | 5/2015 | Miyauchi | G06T 7/0012 |
| | | | 600/438 |
| 2016/0228096 A1* | 8/2016 | Kim | A61B 8/485 |

FOREIGN PATENT DOCUMENTS

| | | |
|---|---|---|
| CN | 101730505 A | 6/2010 |
| JP | 2008-194365 A1 | 8/2008 |
| JP | 2008-272025 A1 | 11/2008 |
| JP | 2009-195613 A1 | 9/2009 |
| JP | 2011-092224 A1 | 5/2011 |
| KR | 20110046328 A * | 5/2011 ............... A61B 8/14 |
| WO | WO 2005/120358 A1 | 12/2005 |
| WO | WO 2011/034005 A1 | 3/2011 |
| WO | WO 2011/102401 A1 | 8/2011 |

OTHER PUBLICATIONS

Combined Office Action and Search Report dated Apr. 3, 2015 in Chinese Patent Application No. 201380001717.1 (with English Translation of Category of Cited Documents).

International Search Report dated Oct. 15, 2013 for PCT/JP2013/074288 filed on Sep. 9, 2013 with English Translation.

Written Opinion dated Oct. 15, 2013 for PCT/JP2013/074288 filed on Sep. 9, 2013.

* cited by examiner

ULTRASONIC DIAGNOSTIC APPARATUS, IMAGE PROCESSING APPARATUS, AND IMAGE PROCESSING METHOD

CROSS-REFERENCE TO RELATED APPLICATIONS

This application is a continuation of PCT international application Ser. No. PCT/JP2013/074288 filed on Sep. 9, 2013 which designates the United States, incorporated herein by reference, and which claims the benefit of priority from Japanese Patent Application No. 2012-198754, filed on Sep. 10, 2012, and Japanese Patent Application No. 2013-186540, filed on Sep. 9, 2013, the entire contents of which are incorporated herein by reference.

FIELD

Embodiments described herein relate generally to an ultrasonic diagnostic apparatus, an image processing apparatus, and an image processing method.

BACKGROUND

In recent years, as a diagnostic imaging technique using an ultrasonic diagnostic apparatus, elastography that visualizes the hardness of a living tissue has been in practical use. In elastography, for example, a stress is applied to a surface of a living tissue by applying and releasing pressure to the tissue with vibration of an ultrasound probe by an operator, and information about strain of the tissue in a living body caused by the stress is calculated from reflected wave data, as harness information.

To calculate information about strain of a tissue (hereinafter, "strain information") in such an ultrasonic diagnostic apparatus, detection of a displacement of the tissue or a moving velocity of the tissue is required. As a method of calculating strain information, a method in which a displacement of a tissue between adjacent frames is detected based on cross-correlation of reception radio frequency (RF) signals of ultrasonic waves, a method in which a moving velocity of a tissue is detected by Doppler method, and a method in which these two methods are combined have been used.

Moreover, provision of reference information to an observer by displaying the reference information has been practiced for an operator to judge whether the strain information calculated by the method is appropriate. The reference information indicates whether pressure and release to a living tissue has been appropriately performed. For example, a method in which a waveform where the vertical axis indicates a mean moving velocity of a tissue in a frame calculated from reception data and the horizontal axis indicates elapsed time is displayed as the reference information has been known.

However, even by referring to the reference information described above, it has been difficult for an operator to properly determine a frame of which time is the appropriate strain information.

DETAILED DESCRIPTION

An ultrasonic diagnostic apparatus according to an embodiment includes a signal processing unit, an indicator calculating unit, a storage unit and a controller. The signal processing unit generates, based on a reflection wave signal of an ultrasonic wave that is transmitted into a subject, a strain information about a strain of a tissue that is pressured and released in the subject in chronological order. The indicator calculating unit calculates an indicator of a state of pressure and release to the tissue at generation of the strain information. The storage unit stores a time phase at generation of the strain information and the indicator at generation of the strain information in an associated manner. The controller extracts a candidate time phase being a time phase of a candidate based on the indicator associated with each of the time phase.

Hereinafter, embodiments of an ultrasonic diagnostic apparatus are explained in detail with reference to the accompanying drawings.

Figure 1:
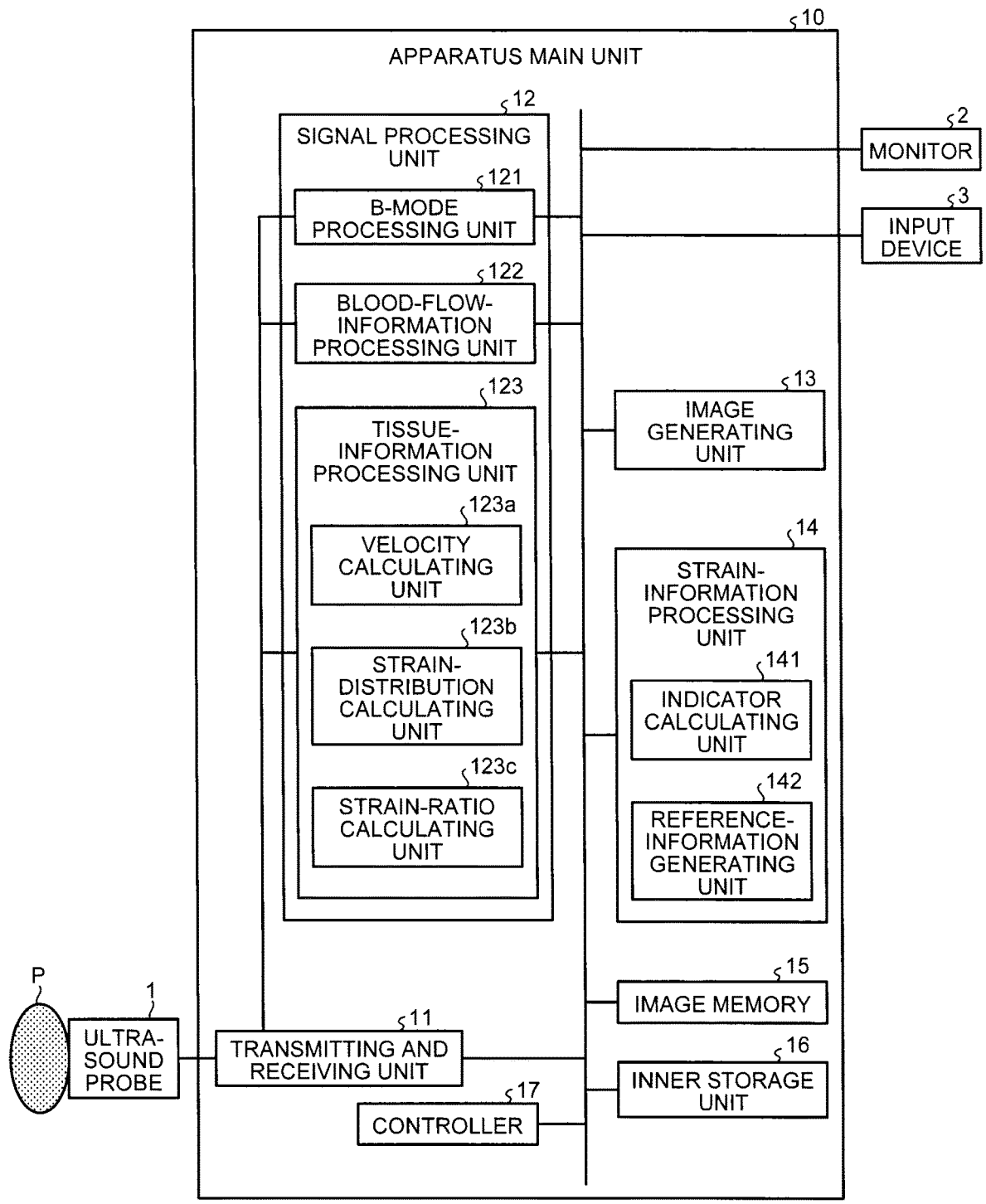
FIG. 1 is a configuration diagram of an ultrasonic diagnostic apparatus according to a first embodiment.

First, a configuration of an ultrasonic diagnostic apparatus according to a first embodiment is explained. FIG. 1 is a configuration diagram of the ultrasonic diagnostic apparatus according to the first embodiment. As shown in FIG. 1, the ultrasonic diagnostic apparatus according to the first embodiment includes an ultrasound probe 1, a monitor 2, an input device 3, and an apparatus main unit 10.

The ultrasound probe 1 is detachably connected to the apparatus main unit 10. The ultrasound probe 1 includes electrically reversible transducer elements and mechanically reversible transducer elements, as ultrasonic transducer elements. For example, the ultrasound probe 1 includes multiple piezoelectric transducer elements. These multiple piezoelectric transducer elements generate ultrasonic waves based on a drive signal provided from a transmitting and receiving unit 11 that is included in the apparatus main unit 10 described later. Furthermore, the ultrasound probe 1 receives reflection waves from a subject P and converts the received reflection waves into electrical signals. Moreover, the ultrasound probe 1 includes a matching layer that is appressed to the piezoelectric transducer elements, a backing member to prevent backward propagation of ultrasonic waves from the piezoelectric transducer elements, and the like.

When ultrasonic waves are transmitted from the ultrasound probe 1 to the subject P, the transmitted ultrasonic waves are reflected successively from surfaces where acoustic impedance is discontinuous on an internal tissue of the subject P, to be received by the piezoelectric transducer elements included in the ultrasound probe 1 as a reflection wave signal. The amplitude of the reflection wave signal to be received is dependent on a difference in acoustic impedance at discontinuous surfaces from which the ultrasonic waves are reflected. The reflection wave signal when a transmitted ultrasonic wave pulse is reflected from a surface of flowing blood, a heart wall, or the like, has a frequency deviation depending on velocity components of a moving body with respect to a transmission direction of the ultrasonic waves by the Doppler effect.

The first embodiment is applicable to any of a case where the ultrasound probe 1 shown in FIG. 1 is a one-dimensional ultrasound probe in which multiple piezoelectric transducer elements are arranged in a single row, a case where the ultrasound probe 1 is a one-dimensional ultrasound probe in which multiple piezoelectric transducer elements arranged in a single row are mechanically swung, and a case where the ultrasound probe 1 is a two-dimensional ultrasound probe in which multiple piezoelectric transducer elements are two-dimensionally arranged in a grid form.

The input device 3 includes a mouse, a keyboard, a button, a panel switch, a touch command screen, a foot switch, a trackball, and the like, receives various setting requests from an operator of the ultrasonic diagnostic apparatus, and transfers the received various setting requests to the apparatus main unit 10.

For example, when a termination button or a freeze button included in the input device 3 is pressed by an operator, transmission and reception of ultrasonic waves are terminated and the ultrasonic diagnostic apparatus according to the first embodiment is suspended. Moreover, for example, when the freeze button is pressed by an operator, the ultrasonic diagnostic apparatus according to the first embodiment shifts from a real-time display mode to a cine-play mode. Furthermore, for example, when an operator rotates the trackball or the like after shifting to the cine-play mode, the ultrasonic diagnostic apparatus according to the first embodiment plays image data of multiple frames stored in a image memory 15 (described later) in a moving image corresponding to the direction of rotation.

The monitor 2 displays a graphical user interface (GUI) for an operator of the ultrasonic diagnostic apparatus to input various setting requests using the input device 3, displays various kinds of image data generated in the apparatus main unit 10, and the like.

The apparatus main unit 10 is a device that generates ultrasonic image data based on reflection waves received by the ultrasound probe 1, and includes the transmitting and receiving unit 11, a signal processing unit 12, an image generating unit 13, a strain-information processing unit 14, the image memory 15, an inner storage unit 16, and a controller 17 as shown in FIG. 1.

The transmitting and receiving unit 11 includes a trigger generating circuit, a transmission delay circuit, and a pulser circuit, and provides a drive signal to the ultrasound probe 1. The pulser circuit repeatedly generates rate pulses to form transmission ultrasonic waves at a frequency of a predetermined rate. Moreover, the transmission delay circuit gives, to each rate pulse generated by the pulser circuit, transmission delay time for each piezoelectric transducer element that is required to determine transmission directivity by focusing ultrasonic waves generated from the ultrasound probe 1 into a beam. Furthermore, the trigger generating circuit applies a drive signal (drive pulses) to the ultrasound probe 1 with timing based on rate pulses. In other words, the transmission delay circuit arbitrarily adjusts the transmission direction from a piezoelectric transducer elements surface by varying the transmission delay time to be given to each rate pulse.

The drive pulses are transmitted from the pulser circuit to the piezoelectric transducer elements in the ultrasound probe 1, and then converted from an electric signal into mechanical vibrations in the piezoelectric transducer elements. The mechanical vibrations are transmitted as ultrasonic waves inside a living body. The ultrasonic waves having transmission delay time varying from one piezoelectric transducer element to another are focused and propagated into predetermined directions. In other words, the transmission delay circuit arbitrarily adjusts the transmission direction from a piezoelectric transducer elements surface by varying the transmission delay time to be given to each rate pulse.

The transmitting and receiving unit 11 has a function of instantly changing a transmission frequency, a transmission driving voltage, and the like to perform a predetermined scanning sequence based on a direction from the controller 17 described later. Particularly, change of the transmission driving voltage is implemented by a transmission circuit of a linear amplifier type that can switch a value of the transmission driving voltage instantly, or by a mechanism for electrically switching among multiple power source units.

Moreover, the transmitting and receiving unit 11 includes an amplifier circuit, an analog/digital (A/D) converter, an adder, and the like, and performs various kinds of processing on a reflection wave signal that is received by the ultrasound probe 1 to generate reflection wave data. The amplifier circuit amplifies the reflection wave signal for each channel to perform gain correction processing. The A/D converter performs A/D conversion on the reflection wave signal that has been gain-corrected, and gives reception delay time that is required to determine reception directivity, to each channel. The adder performs addition processing to generate reflection wave data based on the given reception delay time. By the addition processing performed by the adder, reflection components from the direction corresponding to the reception directivity of the reflection wave signal are enhanced.

As described, the transmitting and receiving unit 11 controls transmission directivity and reception directivity at the time of transmission and reception of ultrasonic waves. The transmitting and receiving unit 11 has a function of instantly changing delay information, a transmission frequency, a transmission driving voltage, the number of aperture elements, and the like according to control by the controller 17 described later. Furthermore, the transmitting and receiving unit 11 can also transmit and receive waveforms varying by frame or by rate.

As for a form of an output signal from the transmitting and receiving unit 11, various forms can be chosen, such as a signal that is called a RF signal including phase information, and amplitude information after envelope detection process.

The signal processing unit 12 is a processing unit that receives reflection data from the transmitting and receiving unit 11 and performs various kinds of signal processing on the received reflection wave data. The signal processing unit 12 includes a B-mode processing unit 121, a blood-flow-information processing unit 122, and a tissue-information processing unit 123 as shown in FIG. 1. The B-mode processing unit 121 receives reflection wave data from the transmitting and receiving unit 11, and performs logarithmic amplification, envelope detection process, and the like on the received reflection wave data, to generate data (B-mode data) in which signal strength is expressed by brightness intensity.

The blood-flow-information processing unit 122 receives reflection wave data from the transmitting and receiving unit 11, and performs frequency analysis on the received reflection wave data, to generate data (blood-flow Doppler data) in which motion information of blood flow in a scanning region based on the Doppler effect is extracted. Specifically, the blood-flow-information processing unit 122 generates the blood-flow Doppler data in which a velocity, a dispersion value, a power value, and the like are extracted as motion information of blood flow being a moving body at multiple points in a two-dimensional space or a three-dimensional space.

The tissue-information processing unit 123 receives reflection wave data from the transmitting and receiving unit 11, and generates information about motion of a tissue being a moving body, using the received reflection wave data. The tissue-information processing unit 123 generates strain information to display the hardness of a living tissue in colors from the reflection wave data when an elastography mode in which elastography is to be performed is designated. Specifically, the tissue-information processing unit 123 generates, based on a reflection wave signal (reflection wave data) of ultrasonic waves that are transmitted into the subject P, strain information about a strain of a tissue to which pressure is applied and released inside the subject P. The tissue-information processing unit 123 generates multiple pieces of strain information in chronological order.

In the elastography mode, for example, application and release of pressure to a tissue are performed by manually vibrating the ultrasound probe 1 that is in contact with a body surface by an operator, to deform the tissue. Furthermore, in the elastography mode, the tissue-information processing unit 123 can generate strain information, for example, based on a tissue deformation caused by subtle hand movement of an operator that holds the ultrasound probe 1.

As a method of generating strain information, a method in which a displacement of a tissue between adjacent frames is detected based on cross-correlation of reception RF signals of ultrasonic waves, a method in which a moving velocity of a tissue is detected by Doppler method (tissue Doppler method), and a method in which these two methods are combined have been known. The tissue-information processing unit 123 can take various methods as a method of calculating strain information.

Moreover, in the elastography mode, a method in which a tissue is deformed by a "push pulse" of a high acoustic pressure that is transmitted from the ultrasound probe 1 can be used. When this method is used, the tissue-information processing unit 123 forms shear waves that are traverse waves propagating through a tissue, and further generates strain information based on a propagation velocity of the shear waves and the like.

A case where application and release of pressure to a tissue are repeatedly performed by manually vibrating the ultrasound probe 1 by an operator, and the tissue-information processing unit 123 generates strain information by tissue Doppler method is explained below. However, the present embodiment is applicable to elastography of all kinds that are practiced by various publicly-known methods including the method described above.

The tissue-information processing unit 123 includes a velocity calculating unit 123a, a strain-distribution calculating unit 123b, and a strain-ratio calculating unit 123c as shown in FIG. 1.

The velocity calculating unit 123a receives reflection wave data from the transmitting and receiving unit 11, and performs frequency analysis on the received reflection wave data, to generate data (tissue Doppler data) in which motion information of a tissue in a scanning area based on the Doppler effect is extracted. Specifically, the velocity calculating unit 123a generates the tissue Doppler data in which a velocity, a dispersion value, and a power value are extracted as motion information of a tissue being a moving body at multiple points in a two-dimensional space or a three-dimensional space. When a tissue Doppler mode is specified, the velocity calculating unit 123a outputs the tissue Doppler data to the image generating unit 13 described later. Furthermore, when the elastography mode is specified, the velocity calculating unit 123a outputs velocity components of the tissue Doppler data to the strain-distribution calculating unit 123b and the like as velocity distribution information.

The strain-distribution calculating unit 123b generates strain distribution that indicates spatial distribution of a strain, as strain information. Specifically, the strain-distribution calculating unit 123b calculates a displacement by performing time integration on velocity components of the velocity distribution information. The strain-distribution calculating unit 123b calculates a local strain of a tissue by performing predetermined calculation (for example, space integration) using the calculated displacement. Further, the strain-distribution calculating unit 123b color-codes values of the calculated local strain of the tissue and maps on corresponding positions to generate the strain distribution information. Because a harder tissue is less deformable, a value of a strain of a hard tissue takes a small value and a value of a strain of a flexible living tissue takes a large value. That is, a value of a strain indicates the hardness (elasticity) of a tissue.

The strain-ratio calculating unit 123c generates, as another strain information, a strain ratio that is calculated from a ratio of strain distributions in predetermined two regions in a space. Specifically, the strain-ratio calculating unit 123c calculates a statistical value of a strain in a reference region to calculate a statistical value of a strain in a target region. The statistical value is, for example, a mean value, a maximum value, a median value, a value of top "n-th" strain, and the like in a region. The value of the top "n-th" strain means an "n-th" largest value among values of strains at respective points assigned in the region, and "n" is a positive integer. For example, the reference region is assigned to a region in which the operator judged that fibrosis has not occurred. Moreover, for example, the target region is assigned to a region in which the operator wishes to measure the degree of fibrosis. The reference region and the target region are explained later. The strain-ratio calculating unit 123c calculates a ratio (strain ratio) of statistical values of strains of these two regions. The strain ratio is defined that the harder one takes the higher value. Therefore, the strain-ratio calculating unit 123c calculates a value by dividing the statistical value (for example, a mean value) of a strain in the reference region by the statistical value (for example, a mean value) of a strain in the target region, as the strain ratio. The strain-ratio calculating unit 123c calculates a strain ratio when the reference region and the target region are designated.

The image generating unit 13 generates ultrasonic image data from data generated by the signal processing unit 12. Specifically, the image generating unit 13 generates, from B-mode data that is generated by the B-mode processing unit 121, B-mode image data in which strength of reflection waves is expressed by brightness. Furthermore, the image generating unit 13 generates, from blood-flow Doppler data generated by the blood-flow-information processing unit 122, velocity image data, dispersion image data, power image data, or blood-flow-Doppler image data as a combination image of these data that indicates motion information of blood flow. Moreover, the image generating unit 13 generates, from tissue Doppler data generated by the velocity calculating unit 123a in the tissue-information processing unit 123, velocity image data, dispersion image data, power image data, or tissue-Doppler image data as a combination image of these data that indicates motion information of a tissue.

The image generating unit 13 then generates image data in which the hardness of a living tissue is displayed in colors, from the strain distribution information generated by the strain-distribution calculating unit 123*b* in the tissue-information processing unit 123. Hereinafter, image data that is generated by the image generating unit 13 in the elastography mode is described as strain image data.

The image generating unit 13 converts (scan conversion) a scan-line signal string of ultrasonic scanning into a scan-line signal string of a video format typified by television and the like, to generate ultrasonic image data as a display image. Furthermore, the image generating unit 13 performs, for example, image processing (smoothing) in which a brightness mean-value image is regenerated, image processing (edge enhancement) using a differentiation filter in an image, and the like, with multiple image frames that have been scan-converted, as various kinds of image processing besides scan conversion.

Moreover, the image generating unit 13 is equipped with a storage memory that stores image data, and can perform reconstruction processing of a three-dimensional image and the like. Furthermore, for example, an image recorded during examination can be retrieved by an operator after diagnosis from the storage memory equipped in the image generating unit 13.

Furthermore, the image generating unit 13 combines character information of various parameters, scales, body marks, and the like with the generated ultrasonic image data, and outputs combined image data to the monitor 2 as a video signal. Moreover, the image generating unit 13 can generate combined image data in which multiple pieces of image data are superimposed. That is, the data generated by the signal processing unit 12 is ultrasonic image data that has not been scan-converted, and the data generated by the image generating unit 13 is ultrasonic image data for display that has been scan-converted. Various kinds of data generated by the signal processing unit 12 are called raw data.

The strain-information processing unit 14 is a processor for processing strain information that is generated by the tissue-information processing unit 123 in the elastography mode. The strain-information processing unit 14 includes an indicator calculating unit 141 and a reference-information generating unit 142 as shown in FIG. 1. Processing performed by the strain-information processing unit 14 according to the first embodiment is explained later in detail.

The image memory 15 is a memory that stores image data generated by the image generating unit 13. For example, the image memory 15 stores a group of ultrasonic image data that corresponds to frames immediately before the freeze button is pressed. The ultrasonic diagnostic apparatus can display ultrasonic moving image by sequentially displaying (cine-display) the images stored in the image memory 15. Furthermore, the image memory 15 can store raw data. The raw data stored in the image memory 15 can be retrieved by an operator after diagnosis, for example, and is to be ultrasonic image data for display through the image generating unit 13.

The image memory 15 according to the present embodiment also stores output results of the strain-information processing unit 14, and this is explained later in detail.

The inner storage unit 16 stores a control program to perform transmission and reception of ultrasonic waves, image processing, and display processing, diagnosis information (for example, patient identification (ID), doctor's findings, and the like), various kinds of data such as a diagnosis protocol and various kinds of body marks. Furthermore, the inner storage unit 16 is also used to store image data that is stored in the image memory 15 and the like as required. Data stored in the inner storage unit 16 can be transferred to a peripheral device outside the apparatus through an interface circuit not shown.

The controller 17 controls the entire processing in the ultrasonic diagnostic apparatus. Specifically, the controller 17 controls processing of the transmitting and receiving unit 11, the signal processing unit 12, the image generating unit 13, and the strain-information processing unit 14 based on various setting requests input by an operator through the input device 3, and on various control programs and various kinds of data that are retrieved from the inner storage unit 16. Moreover, the controller 17 controls to display ultrasonic image data stored in the image memory 15 and the like on the monitor 2.

As described above, the entire configuration of the ultrasonic diagnostic apparatus according to the first embodiment has been explained. With the configuration, the ultrasonic diagnostic apparatus according to the first embodiment performs elastography.

Conventionally, to judge whether strain information (strain distribution information) generated by the tissue-information processing unit 123 is appropriate, the ultrasonic diagnostic apparatus generates reference information explained below to display on the monitor 2. The reference information is, for example, a waveform in which a tissue mean moving-velocity in a displayed frame of strain image data that is being displayed in real time on the monitor 2 is plotted on the vertical axis, and elapsed time is plotted on the horizontal axis. The mean moving velocity (tissue mean moving velocity) is to be an indicator of a state of application and release of pressure to a tissue at the time of generating strain information. Furthermore, the displayed frame of the strain image data is a region that actually indicates strain distribution on the monitor 2 among regions that are scanned to generate the strain image data.

In a conventional technique, for example, the indicator calculating unit 141 shown in FIG. 1 calculates, in real time, a mean moving velocity from velocity distribution information output by the velocity calculating unit 123*a* in a region of the strain image data that is displayed on the monitor 2. Moreover, in a conventional technique, for example, the reference-information generating unit 142 shown in FIG. 1 generates, in real time, reference information that is a waveform by plotting mean moving velocities along the time axis. Further, in a conventional technique, the monitor 2 displays the reference information in real time by the control of the controller 17.

Furthermore, in a conventional technique, an operator refers to the reference information that is displayed in real time and presses the freeze button, for example, upon determining that appropriate application and release of pressure has been performed. The operator thereby brings a screen into a freezed state. When the freeze button is pressed, the image memory 15 stores multiple image frames of a predetermined past period from the moment of depression of the freeze button by the control of the controller 17 for performing cine-play, so that the image frames are not overwritten by other data. The operator plays the frames of the strain image data stored in the image memory 15 in a moving image, and refers to the moving image. Thus, the operator chooses strain image data that is considered to be appropriate for diagnosis.

However, it has been difficult for an operator to judge a frame of which time is the frame in which appropriate strain distribution information is extracted, even by referring to the above reference information. This problem is explained using FIG. 2, FIG. 3A, FIG. 3B, FIG. 3C, and FIG. 4. FIG. 2, FIG. 3A, FIG. 3B, FIG. 3C, and FIG. 4 are diagrams for explaining problems in a conventional technique.

Figure 2:
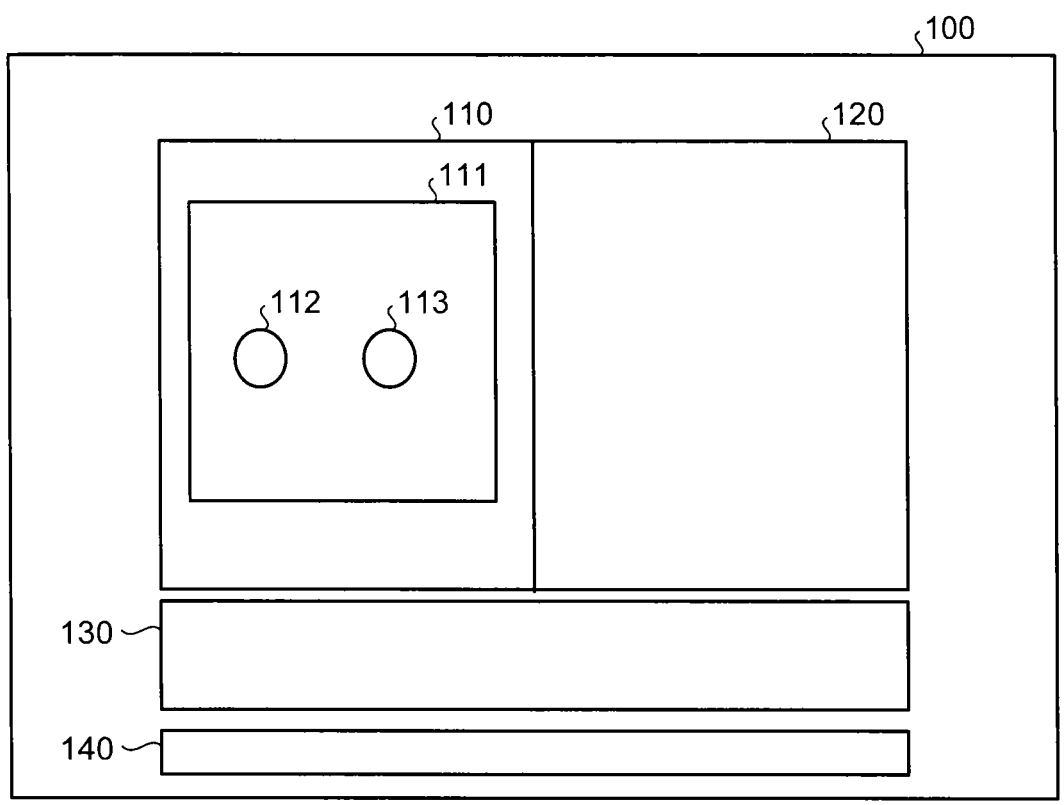
FIG. 2, FIG. 3A, FIG. 3B, FIG. 3C and FIG. 4 are diagrams for explaining problems in conventional techniques.

FIG. 2 shows an example of a conventional display screen on which the reference information is displayed. In one example shown in FIG. 2, a B-mode-strain-distribution superimposition display-region 110 and a B-mode display region 120 are arranged in parallel in an entire screen 100. Moreover, in the example shown in FIG. 2, a reference-information display region 130 is arranged under these two display regions in the entire screen 100, and a strain-ratio display region 140 is arranged under the reference-information display region 130.

The B-mode display region 120 is a region in a part of which B-mode image data of the same scanning region that is generated from reflection wave data used for generating strain image data is displayed. The B-mode-strain-distribution superimposition display-region 110 is a region in a part of which strain image data is displayed. The B-mode-strain-distribution superimposition display-region 110 has a strain-distribution display region 111 therein. The strain-distribution display region 111 is a region in which strain distribution of strain image data is displayed. In the strain-distribution display region 111, together with the strain distribution information, B-mode image data of the same region can be superimposed to be displayed at predetermined transparency.

Furthermore, in the strain-distribution display region 111, regions for calculating a strain ratio by the strain-ratio calculating unit 123c described above are designated by an operator. For example, 112 shown in FIG. 2 is the reference region described above and 113 shown in FIG. 2 is the target region described above. A strain ratio calculated by the strain-ratio calculating unit 123c is displayed in the strain-ratio display region 140.

The reference-information display region 130 is a region in which reference information that is generated by the reference-information generating unit 142 is displayed. The reference information is given in a waveform in which mean moving velocities of respective frames calculated by the indicator calculating unit 141 are plotted along the time axis.

Figure 3A:
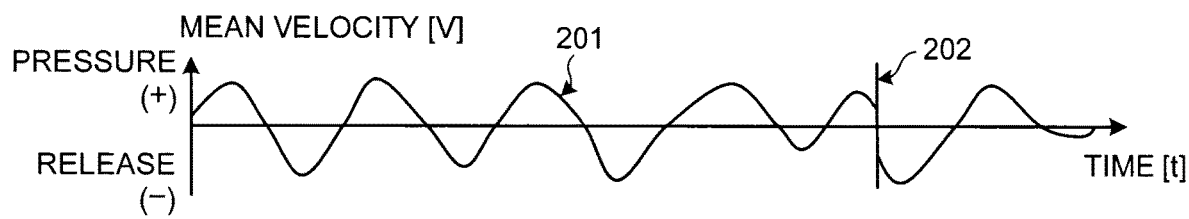
Figure 3B:
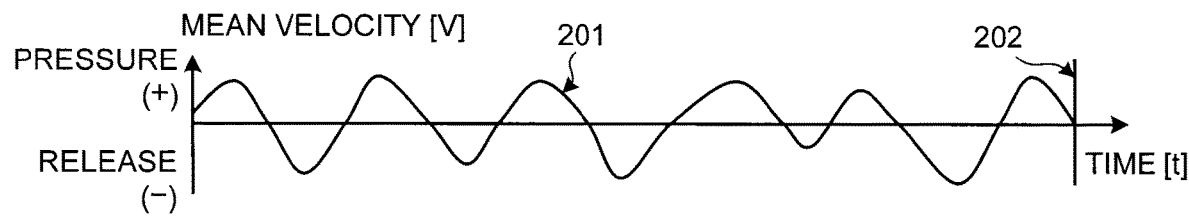
Figure 3C:
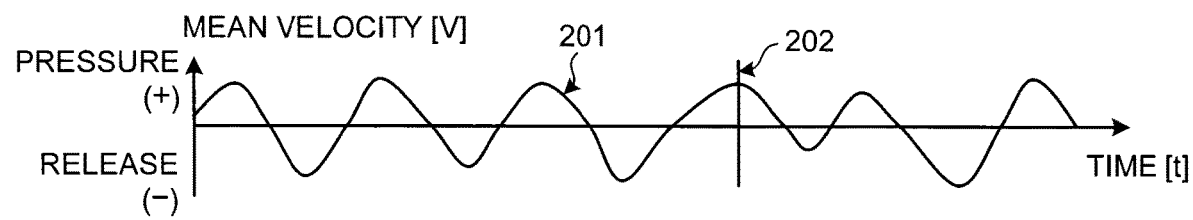

FIG. 3A shows an example of the reference information that is displayed in the reference-information display region 130 at real-time display. FIG. 3B shows an example of the reference information that is displayed in the reference-information display region 130 when the freeze button is pressed. FIG. 3C shows an example of the reference information that is displayed in the reference-information display region 130 at cine-playing after the freeze button is pressed. 201 shown in FIG. 3A, FIG. 3B, and FIG. 3C indicates a waveform of the tissue mean moving velocity, and 202 indicates a time axis cursor displayed on the monitor 2. Furthermore, the horizontal axis shown in FIG. 3A, FIG. 3B, and FIG. 3C is the time axis indicating time (t) at a point at which each frame is generated. That is, the horizontal axis shown in FIG. 3A, FIG. 3B, and FIG. 3C indicates the time phase when each frame is generated. The scale and the length of the horizontal axis are determined based on a frame rate at which the strain image data is generated and a memory capacity assigned for cine-play in the image memory 15.

In the waveform 201 of the tissue mean moving velocity shown in FIG. 3A, FIG. 3B, and FIG. 3C, when a mean velocity (V), which is the tissue mean moving velocity, takes a positive value, it is indicated that the tissue is "pressured", and when the mean velocity (V) takes a negative value, it is indicated that the tissue is "released". The waveform 201 of the tissue mean moving velocity is an indicator to judge the appropriateness in application and release of pressure for each frame, that is, the appropriateness of strain information. For example, when the absolute value of the tissue mean moving velocity is larger, it can be determined that the strain information is more appropriate.

In the real-time display mode, the time axis cursor 202 shown in FIG. 3A is arranged at a position indicating the time phase of the latest frame displayed on the current monitor 2. In the real-time display mode, an operator can grasp a value of the latest mean velocity that is updated in real time, by referring to the time axis cursor 202. By the time axis cursor 202, the reference information is updated.

When the freeze button is pressed, the time axis cursor 202 moves to the frame at the point of transition to the cine-play mode, that is, the right end point of the waveform 201.

In the cine-play mode, for example, the controller 17 retrieves strain image data of a past time phase and the like from the image memory 15 to display on the monitor 2 based on rotation of the trackball. In the cine-play mode, the time axis cursor 202 is displayed, on the time axis as shown in FIG. 3C, at a position corresponding to the past time phase being displayed.

Figure 4:
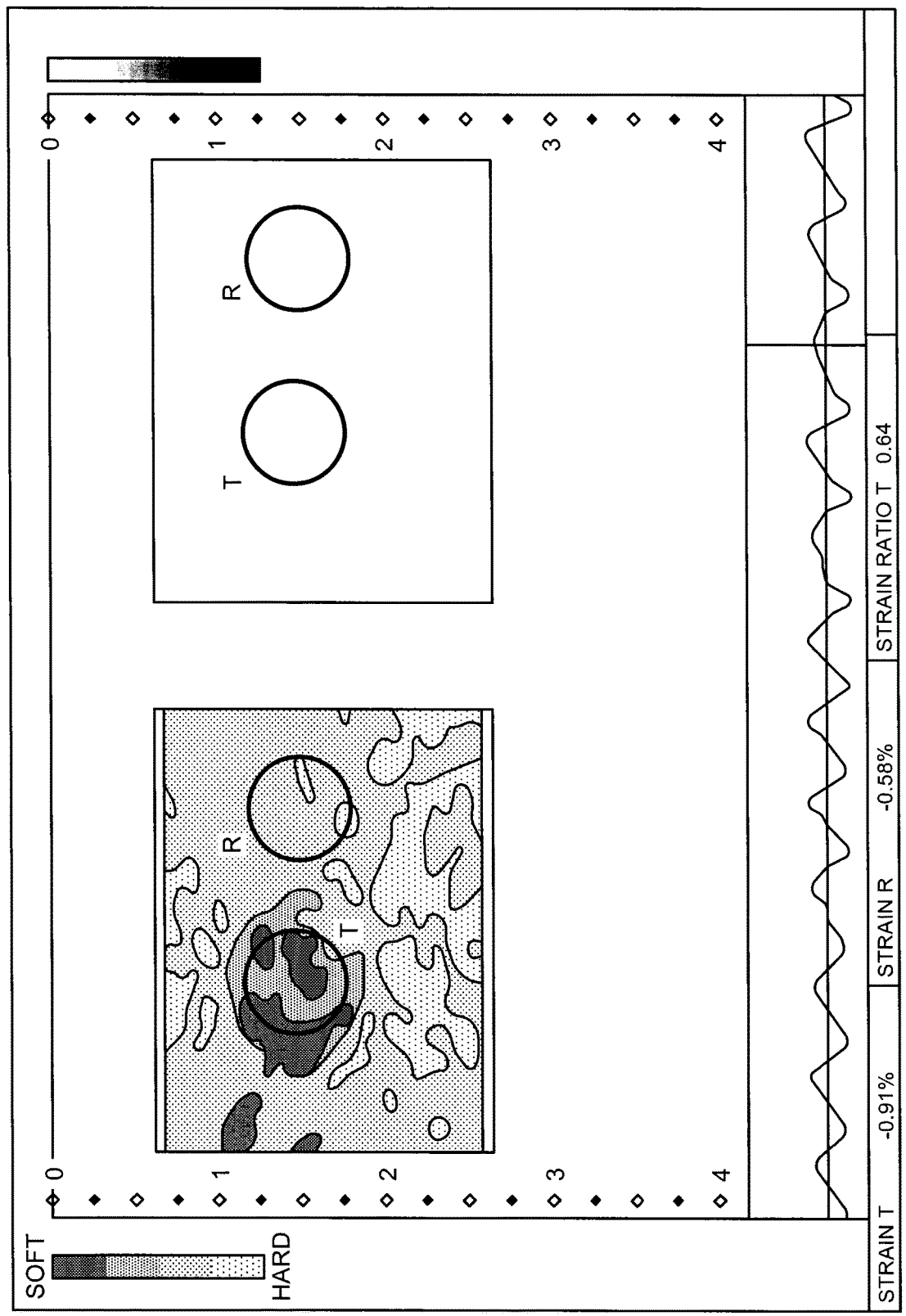

FIG. 4 shows an example of a screen displayed on the monitor 2 in the cine-play mode. As shown in FIG. 4, in the display screen of the monitor 2, a part of a frame of the strain image data is displayed on the left side together with a color bar that indicates the degree of strain (hardness) corresponding to colors rendered in the strain distribution information, and a part of a frame of the B-mode image data of the same time phase as that of the strain image data is displayed on the right side. On the right side of the B-mode image data, a grayscale bar indicating the magnitude of brightness value is displayed as shown in FIG. 4. Furthermore, in the strain image data, a circle (refer to R in the figure) indicating the reference region and a circle (refer to T in the figure) indicating the target region are displayed. Moreover, in the B-mode image data also, a circle (refer to R in the figure) indicating the reference region and a circle (refer to T in the figure) indicating the target region are displayed. In the example shown in FIG. 4, a case where the B-mode image data is not displayed is shown.

Furthermore, as shown in FIG. 4, the monitor 2 displays a waveform being the reference information with the time axis cursor under the display region for the strain image data and the display region for the B-mode image data. The time axis cursor shown in FIG. 4 indicates the time phase of the displayed past frame. Moreover, the monitor 2 displays the mean strain "Strain T: −0.91%" of the target region, the mean strain "Strain R: −0.58%" of the reference region, and the strain ratio "Strain Ratio T: 0.64" under the reference information. The forms of display shown in FIG. 2 and FIG. 4 are just one example. For example, when the reference region and the target region are not designated, the controller 17 is not necessarily required to arrange the strain-ratio display region 140. Alternatively, when the reference region and the target region are not designated, the controller 17 can control not to display character information in the strain-ratio display region 140.

However, even if an operator refers to the reference information displayed on the screen shown in FIG. 4, the operator cannot judge whether the frame corresponding to the position of the displayed time axis cursor is optimal at first sight.

Therefore, the ultrasonic diagnostic apparatus according to the first embodiment performs processing explained below for an operator to be able to acquire appropriate information about strain easily.

First, the indicator calculating unit 141 calculates an indicator of a state of pressure and release of a tissue at the time of generation of the strain information. The indicator calculating unit 141 performs indicator calculation processing at predetermined time intervals. As one example, the indicator calculating unit 141 performs the indicator calculation processing every time the strain information is generated at predetermined intervals. The predetermined interval is determined, for example, from the frame rate of strain image data. Alternatively, the indicator calculating unit 141 performs the indicator calculation processing at preset time intervals. For example, the indicator calculating unit 141 performs the indicator calculation processing every second or every two seconds. Furthermore, for example, the indicator calculating unit 141 according to the first embodiment calculates a statistical value of a velocity of a tissue from distribution of the velocity information that is calculated by the velocity calculating unit 123*a*, as an indicator. The statistical value is a mean value, a maximum value, and a median value of a velocity of a tissue, a value of the top "n-th" velocity of a tissue, and the like. The value of the top "n-th" velocity signifies an "n-th" largest value among values of velocities at respective points assigned in the region, and "n" is a positive integer. Hereafter, a case where the indicator calculating unit 141 calculates a mean velocity of a tissue from a distribution of the velocity information that is calculated by the velocity calculating unit 123*a* as an indicator is explained. The mean velocity herein is a mean velocity of a tissue in the region for which a strain distribution is actually being displayed on the monitor 2 among strain image data. That is, the indicator calculating unit 141 according to the first embodiment calculates a tissue mean moving velocity as an indicator, similarly to the conventional technique describe above. Furthermore, the region to be a subject of indicator calculation is, for example, a region of interest including an entire tissue for which the degree of fibrosis is wished to be diagnosed or a region including a part of the tissue is included, and is the strain distribution display region 111 shown in FIG. 2. The reference region and the target region described above are regions that are allocated in the region of interest. However, the present embodiment is applicable to a case where a statistical value of a velocity of a tissue in the region of interest is used as an indicator, other than the mean velocity of a tissue.

The reference-information generating unit 142 according to the first embodiment generates an indicator of a state of pressure and release as the reference information that is composed of a chronological waveform. That is, the reference-information generating unit 142 according to the first embodiment generates a waveform of a tissue mean moving velocity as the reference information, similarly to the conventional technique described above. The present embodiment is also applicable to a case where a waveform of another statistical value, such as a waveform of a maximum moving velocity of a tissue, is generated as the reference information.

The image memory 15 according to the first embodiment stores a time phase at the time of generation of the strain information and the indicator at the time of generation of the strain information in an associated manner. Specifically, the image memory 15 according to the first embodiment further stores image data based on the strain information associating with the time phase and the indicator at the time of generation of the strain information. More specifically, the image memory 15 stores an indicator that is calculated at predetermined time intervals associating with image data based on the strain information that is generated at the time of calculation of the indicator. In the first embodiment, the image memory 15 also stores a tissue mean moving velocity as a statistical value of a moving velocity of the tissue at the time of generation of respective strain image data, when storing multiple pieces of strain image data based on multiple pieces of strain distribution information that are generated in chronologically. The first embodiment is applicable to a case where the reference-information generating unit 142 stores a tissue mean moving velocity and time information (time phase) of the tissue mean moving velocity in an associated manner, and the image memory 15 stores the strain image data and the time information (time phase) of the strain image data in an associated manner. In other words, in the first embodiment, as long as a value of an indicator at the time of generation of strain image data can be identified, various forms of storage can be taken.

The controller 17 according to the first embodiment extracts a candidate time phase that is a time phase being a candidate, based on an indicator associated with each time phase. The candidate time phase indicates a time phase of a candidate for diagnosis. Moreover, the candidate time phase indicates a time phase of information relating to the strain information such as image data (strain image data) being a candidate to be displayed for presenting to an operator for diagnosis. The controller 17 according to the first embodiment controls to display at least one of information about the candidate time phase and information relating to the strain information of the candidate time phase on the monitor 2. For example, the controller 17 according to the first embodiment performs extraction processing of a candidate time phase, upon receiving a request to display an image data group stored in the image memory 15 from an operator, based on an indicator associated with each image data that composes the image data group. The controller 17 then controls to display, on the monitor 2, information relating to the image data of the candidate time phase, that is, information about the image data being a display candidate. The image memory 15 stores, by the control of the controller 17, multiple frames of a predetermined past period from the moment of depression of the freeze button together with the reference information to perform cine-play, so as not to be overwritten by other data. In the first embodiment, various data for cine-play can be stored in the inner storage unit 16 or in a storage unit that is arrange separately for cine-play.

The controller 17 according to the first embodiment ranks and extracts multiple candidate time phases based on an indicator associated with each time phase. In other words, the controller 17 ranks and chooses multiple pieces of image data to be a display candidate based on an indicator associated with each image data composing the image data group. Specifically, the controller 17 according to the first embodiment controls to display, in the reference information, information indicating a candidate time phase, that is, information indicating a time phase of image data to be a display candidate upon receiving a request to display an image data group stored in the image memory 15 from an operator. The information indicating a candidate time phase (information indicating a time phase of image data to be a display candidate) is explained later.

Namely, when the freeze button is pressed, the controller 17 according to the first embodiment ranks and chooses multiple pieces of strain image data to be a display candidate based on the tissue mean moving velocity that is associated with each strain image data stored in the image memory 15. The controller 17 according to the first embodiment controls to display time axis cursors corresponding to respective time phases of multiple pieces of strain image data that are chosen as a display candidate, in the reference information in a superimposed manner. The extraction processing of a candidate time phase performed by the controller 17 is described as choosing processing of a candidate time phase in some cases below.

Figure 5:
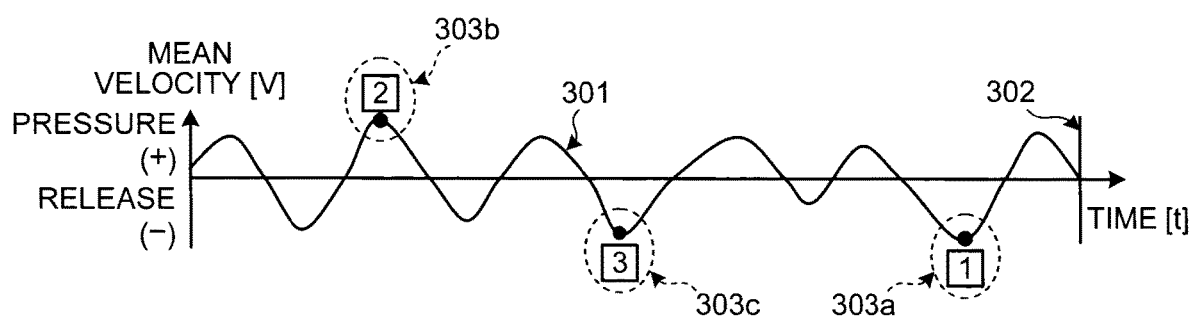
FIG. 5, FIG. 6 and FIG. 7 are diagrams showing an example of display control performed by a controller according to the first embodiment.
Figure 6:
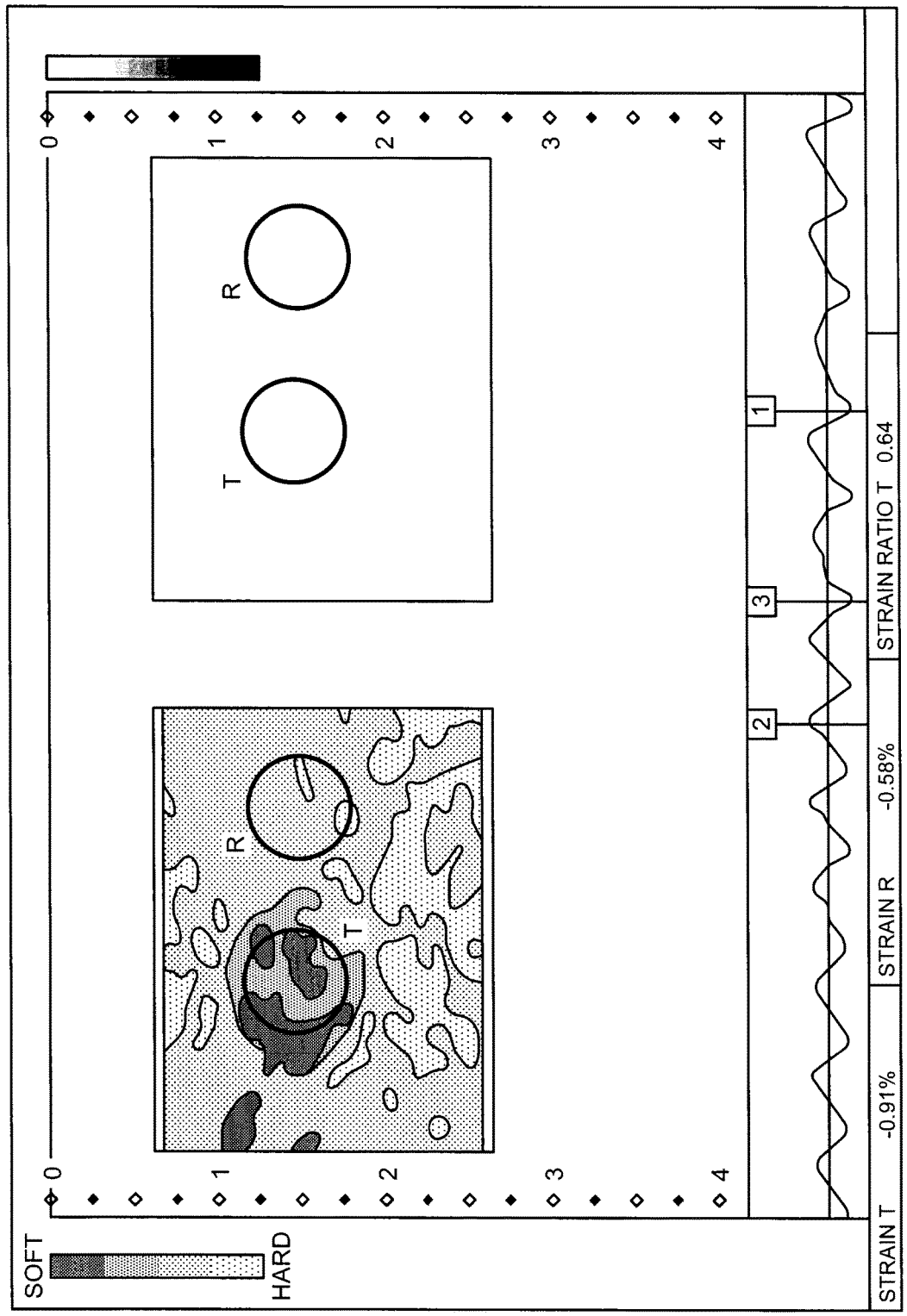
Figure 7:
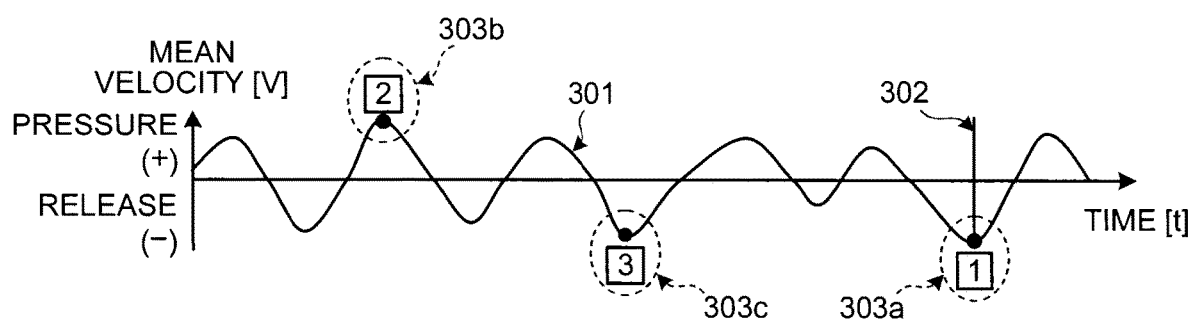

An example of the display control processing of the controller 17 described above is explained below using FIG. 5 to FIG. 7. FIG. 5 to FIG. 7 are diagrams showing an example of the display control performed by the controller 17 according to the first embodiment. Explanation is given below supposing that the display screen in which the reference information is displayed takes the similar form as the conventional example shown in FIG. 2.

In FIG. 5, an example of the reference information displayed on the monitor 2 when the freeze button is pressed is shown. In the first embodiment also, the strain distribution information of a frame at the time of transition to the cine-play mode is displayed. At the time when the freeze button is pressed, a time axis cursor 302 moves, similarly to the example shown in FIG. 3B, to the frame at the time of transition to the cine-play mode, that is, the right end point in a waveform 301 of the tissue mean moving velocity (refer to FIG. 5).

In the first embodiment, for example, the controller 17 chooses top three tissue mean moving velocities having largest absolute values. As an example, the controller 17 specifies a peak of the waveform 301 of a tissue mean moving velocity in a pressure area and a release area excluding an area in which the tissue mean moving velocity is in the vicinity of "0". The controller 17 then ranks frames based on the magnitude of the absolute values of the tissue mean moving velocity. The controller 17 then displays three markers (marker 303a, marker 303b, and marker 303c) that indicate positions of three tissue mean moving velocities ranked top three in the waveform 301, ordinal ranks and time phases of the three tissue mean moving velocities ranked top three. That is, the controller 17 controls to display, together with information indicating a time phase of strain image data to be a display candidate, information about the ordinal rank of the image data in the reference information. In other words, the controller 17 controls to further display, together with information indicating a candidate time phase, information about the ordinal rank of a candidate time phase in the reference information.

The marker 303a is a marker indicating that the absolute value is the first rank, and is formed with a character "1" and a black dot on a waveform as shown in FIG. 5. Moreover, the marker 303b is a marker indicating that the absolute value is the second rank, and is formed with a character "2" and a black dot on a waveform as shown in FIG. 5. Furthermore, the marker 303c is a marker indicating that the absolute value is the third rank, and is formed with a character "3" and a black dot on a waveform as shown in FIG. 5.

In the above choosing processing, the controller 17 can perform ranking based only on the absolute value of the tissue mean moving velocity simply without performing the processing to specify the pressure area and the release area excluding the area in which the tissue mean moving velocity is in the vicinity of "0". Furthermore, in the above choosing processing, the controller 17 can perform ranking of frames limiting in the pressure area, or in the release area. In addition, for example, the number of candidates to be presented to an operator can be arbitrarily changed by the operator.

By the display control, the monitor 2 displays three markers on a waveform as shown in FIG. 6. In the example shown in FIG. 6, instead of black dots shown in FIG. 5, line segments similar to the time axis cursor are used as the markers. As it is obvious when compared with the conventional example shown in FIG. 4, an operator can grasp information about a candidate time phase by referring to the screen shown in FIG. 6, and can judge a frame of which time is appropriate strain information easily.

The controller 17 according to the first embodiment controls to display multiple pieces of image data corresponding to the candidate time phases on the monitor 2 in predetermined order (rank order or temporal order) according to a predetermined operation performed by an operator. In other words, the controller 17 controls to display multiple pieces of chosen image data (multiple pieces of strain image data) on the monitor 2 in predetermined order (rank order or temporal order) based on a predetermined operation performed by an operator.

Specifically, in the first embodiment, in the cine-play mode, strain image data of the frames of top ranks is retrieved from the image memory 15 and displayed on the monitor 2, for example, according to rotation of the trackball by an operator.

When the predetermined order is the rank order, the frames to be displayed according to rotation of the trackball is "the frame corresponding to the position of the marker 303a, the frame corresponding to the position of the marker 303b, and then the frame corresponding to the position of the marker 303c". When the predetermined order is the temporal order, the frames to be displayed according to rotation of the trackball is "the frame corresponding to the position of the marker 303a, the frame corresponding to the position of the marker 303c, and then the frame corresponding to the position of the marker 303b". When the direction of rotation is reversed, the order of display is reversed.

For example, when "the frame corresponding to the position of the marker 303a" is displayed, the position of the time axis cursor 302 moves to the position of the marker 303a on the monitor 2 by the control of the controller 17. An operator can understand that the strain image data for which the indicator of the first rank is calculated is being displayed by referring to the reference information shown in FIG. 7. In the first embodiment, for example, the strain ratio is re-calculated to be displayed for the frame that is currently displayed regardless of the real-time display mode or the cine-play mode.

Figure 8:
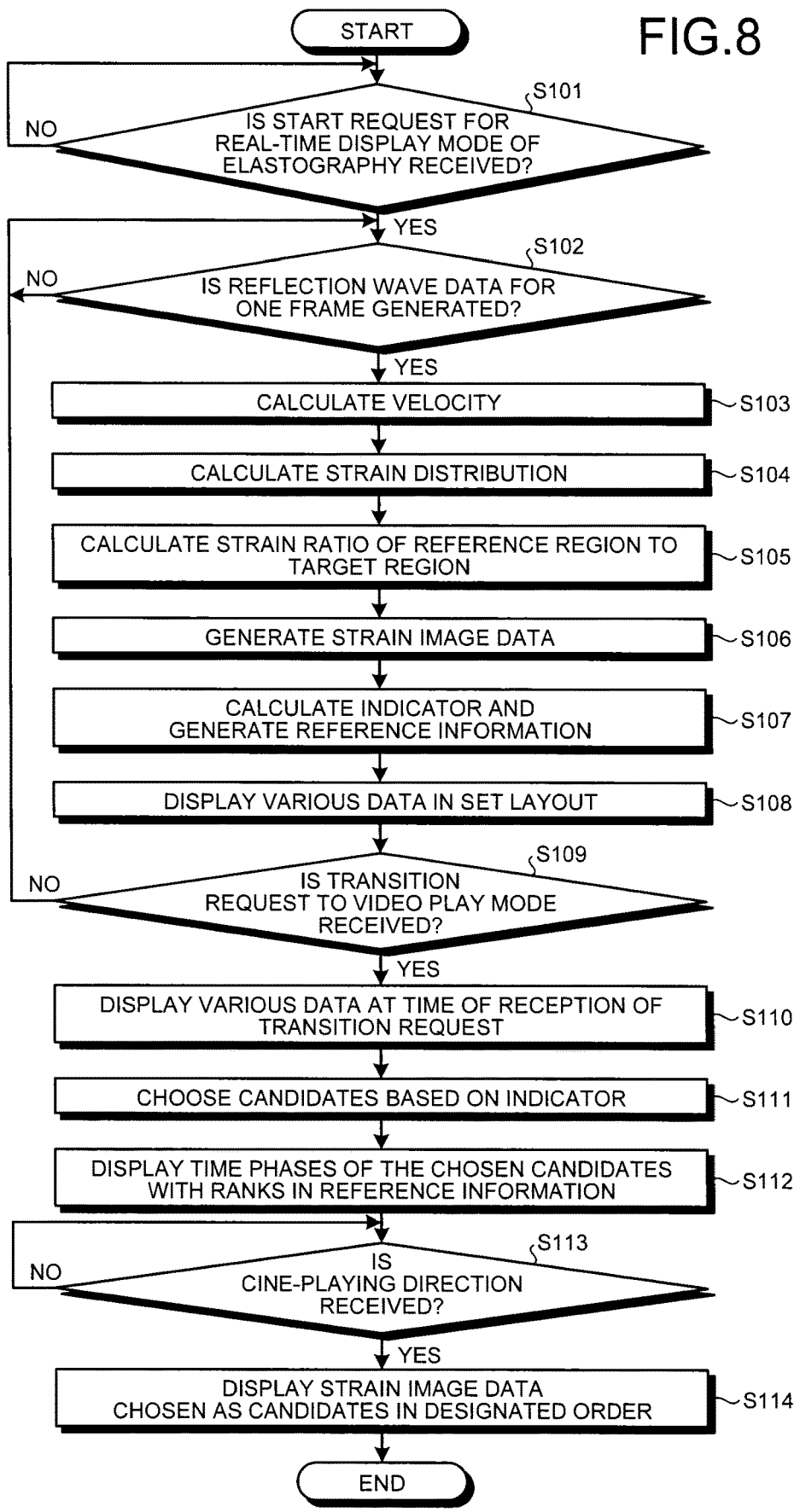
FIG. 8 is a flowchart for explaining a processing example of the ultrasonic diagnostic apparatus according to the first embodiment.

Next, a processing example of the ultrasonic diagnostic apparatus according to the first embodiment is explained using FIG. 8. FIG. 8 is a flowchart for explaining a processing example of the ultrasonic diagnostic apparatus according to the first embodiment.

As shown in FIG. 8, the controller 17 of the ultrasonic diagnostic apparatus according to the first embodiment determines whether a request to start the real-time display mode of elastography has been received (step S101). When the request to start the real-time display mode has not been received (step S101: NO), the controller 17 waits until a request to start the real-time display mode is received.

On the other hand, when a request to start the real-time display mode of elastography has been received (step S101:

YES), the controller 17 starts processing in the elastography mode. The controller 17 then determines whether reflection wave data for one frame has been generated (step S102). When reflection wave data for one frame has not been generated (step S102: NO), the controller 17 waits until reflection wave data for one frame is generated.

On the other hand, when reflection wave data for one frame has been generated (step S102: YES), by the control of the controller 17, the velocity calculating unit 123a calculates a velocity (velocity distribution information) (step S103), and the strain-distribution calculating unit 123b calculates a strain distribution (strain distribution information) (step S104). Furthermore, when regions are designated, the strain-ratio calculating unit 123c calculates a strain ratio of the reference region to the target region (step S105).

The image generating unit 13 generates strain image data (step S106). The indicator calculating unit 141 calculates an indicator (a mean velocity of a tissue in the present embodiment) and the reference-information generating unit 142 generates the reference information (step S107). When parallel display of B-mode image data is performed, the ultrasonic diagnostic apparatus performs generation of B-mode image data in parallel with the processing from step S103 to step S106. Moreover, in the present embodiment, the ultrasonic diagnostic apparatus can perform generation of tissue-Doppler image data for display in parallel with the processing from step S103 to step S106.

The monitor 2 displays various kinds of data in a set layout by the control of the controller 17 (step S108, refer to FIG. 2 and the like). The image memory 15 stores the image data displayed at step S108 associating with the indicator.

The controller 17 determines whether a request to transit to a video play mode has been received (step S109). Specifically, the controller 17 determines whether the freeze button is pressed. When a request to transit to the video play mode has not been received (step S109: NO), the controller 17 determines whether reflection wave data has been generated, returning to step S102.

On the other hand, when a request to transit to the video play mode has been received (step S109: YES), the monitor 2 displays various kinds of data at the time of reception of the transit request by the control of the controller 17 (step S110). When it is YES at step S109, the controller 17 controls to store an indicator and image data of a predetermined period (predetermined past period) so as not to be overwritten.

The controller 17 then chooses multiple candidates based on the indicator of the predetermined period (step S111), and controls to display information indicating time phases of the chosen candidates together with the ranks in the reference information (step S112).

The controller 17 then determined whether a cine-playing direction has been received (step S113). When a cine-playing direction has not been received (step S113: NO), the controller 17 waits until a cine-playing direction is received.

On the other hand, when a cine-playing direction has been received (step S113: YES), the monitor 2 displays multiple pieces of strain image data that are chosen as multiple candidates in designated order by the control of the controller 17 (step S114), and the processing is ended.

As described above, in the first embodiment, a candidate time phase is chosen for which pressure and release are determined to be appropriate based on an objective indicator, and the chosen candidate time phase is displayed to an operator. The candidate time phase is a time phase of an area other than a transition area from pressure to release and a transition area from release to pressure, and is a time phase where the stress by releasing pressure or the stress by applying pressure is approximately maximum. Because a candidate time phase is provided, an operator can promptly refer to the strain image data of the frame corresponding to the candidate time phase. For example, the frame corresponding to the candidate time phase and frames adjacent to the frame can be referred to. Therefore, in the first embodiment, an operator can easily obtain appropriate information relating to a strain.

Moreover, in the first embodiment, multiple candidate time phases are chosen (extracted) after being ranked, and the multiple candidate time phases are displayed to an operator. Therefore, in the first embodiment, an operator can easily choose a frame in which appropriate strain information is visualized.

Furthermore, in the first embodiment, respective pieces of image data of multiple candidate time phases are sequentially displayed by a simple operation performed by an operator. By this processing, in the first embodiment, an operator can choose a frame in which appropriate strain information is visualized further easily. The first embodiment is applicable to either a case where only information about a candidate time phase is displayed, or a case where only image data (strain image data) of a candidate time phase is displayed. Moreover, the first embodiment is applicable to either a case where strain image data of a candidate time phase is displayed as information relating to strain information of the candidate time phase, a case where the strain image data of the candidate time phase and a value relating to the strain information of the candidate time phase are displayed, or a case where both of these are displayed. The value relating to the strain information of the candidate time phase is, for example, a statistical value of a displacement in the target region, or a statistical value of respective displacements in the target region and the reference region. Furthermore, the value relating to strain information of the candidate time phase is, for example, a statistical value of a strain in the target region, or a statistical value of respective strains in the target region and the reference region. Furthermore, the value relating to the strain information is, for example, the strain ratio of the target region and the reference region.

In the first embodiment, a case where a statistical value (for example, mean value) of a velocity (moving velocity) of a tissue is used as an indicator has been explained. However, in the first embodiment, a statistical value of a displacement of a tissue can be used as an indicator. The statistical value of a displacement of a tissue is a mean value, a maximum value, and a median value of a displacement, a value of the top "n-th" displacement, and the like in a region of interest. The value of the top "n-th" displacement signifies an "n-th" largest value among values of displacements at respective points assigned in the region, and "n" is a positive integer. Because a displacement of a tissue is a value that is calculated in the process of calculation of strain by the strain-distribution calculating unit 123b, the indicator calculating unit 141 can calculate, for example, a mean displacement in the strain-distribution display region 111. Moreover, in the first embodiment, a statistical value of a strain of a tissue can be used as an indicator. The statistical value of a strain of a tissue is a mean value, a maximum value, and a median value, the top "n-th" value of a strain, and the like in a region of interest. The value of the top "n-th" strain signifies an "n-th" largest value among values of strains at respective points assigned in the region, and "n" is a positive integer. In this case, the indicator calculating unit 141 calculates, for example, a mean strain in the strain-distribution display region 111 from the strain distribution information calculated by the strain-distribution calculating unit 123b. Furthermore, in the first embodiment, a statistical value of a strain ratio of in two regions of a tissue can be used as an indicator. The two regions are, for example, the reference region and the target region. The statistical value of a strain ratio is a ratio of a mean strain value in the reference region to a mean strain value in the target region, a ratio of a maximum strain value in the reference region to a maximum strain value in the target region, and a ratio of a median strain value in the reference region to a median strain value in the target region, a ratio of the top "n-th" strain value in the reference region to the top "n-th" strain value in the target region, and the like. In this case, the indicator calculating unit 141 outputs data output by the strain-ratio calculating unit 123c to the reference-information generating unit 142 as an indicator.

Moreover, in the first embodiment, a statistical displacement of a tissue, a statistical velocity, a statistical strain, and a statistical strain ratio can be calculated in combination, and a candidate time phase can be chosen (extracted) using these indicators. As described, in the first embodiment, the indicator calculating unit 141 can calculate at least one of a statistical displacement value of a tissue, a statistical velocity value of a tissue, a statistical stain value of a tissue, and a statistical value of a strain ratio of two regions of a tissue, as an indicator.

Figure 9A:
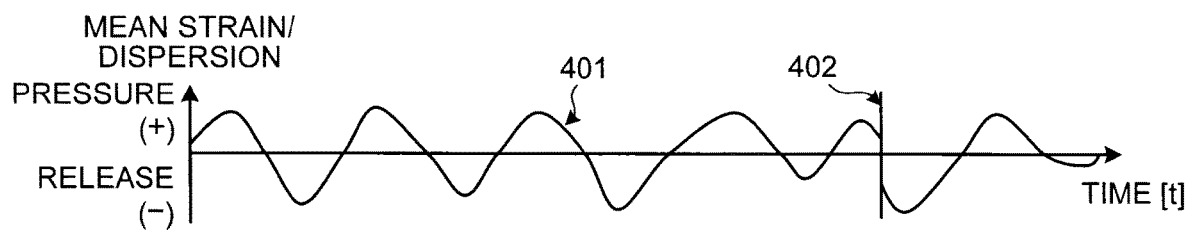
FIG. 9A, FIG. 9B and FIG. 9C are diagrams for explaining a second embodiment.
Figure 9B:
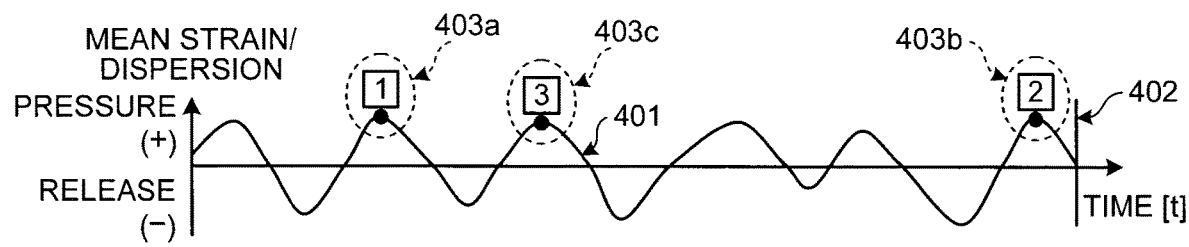
Figure 9C:
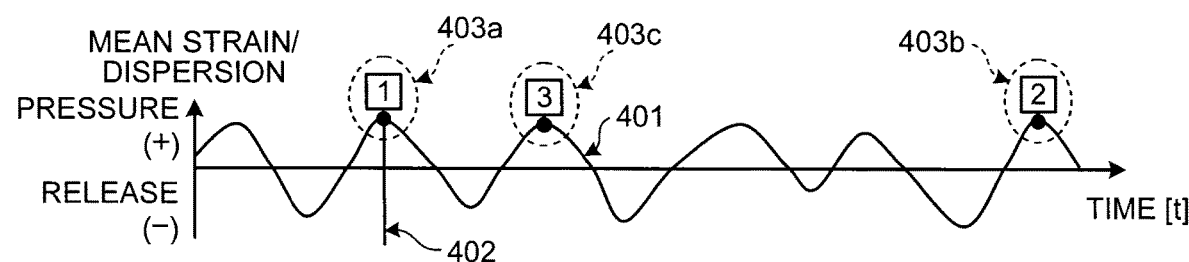

While a case where a mean velocity of a tissue is used as an indicator has been explained in the first embodiment as an example, in a second embodiment, a case where a statistical value and a dispersion of a strain of a tissue are used as an indicator is explained using FIG. 9A, FIG. 9B, and FIG. 9C. FIG. 9A, FIG. 9B, and FIG. 9C are diagrams for explaining the second embodiment.

An ultrasonic diagnostic apparatus according to the second embodiment is configured similarly to the ultrasonic diagnostic apparatus according to the first embodiment shown in FIG. 1. However, the indicator calculating unit 141 according to the second embodiment calculates a statistical value and a dispersion of a strain of a tissue as an indicator. The statistical value of a strain of a tissue is a mean value, a maximum value, a median value and the like of a strain of a tissue as explained in the first embodiment. This is mainly explained below. Except the content explained below, the contents explained in the first embodiment are applicable to the second embodiment also. Hereinafter, a case where the indicator calculating unit 141 calculates a mean value and a dispersion of a strain of a tissue is explained.

The indicator calculating unit 141 calculates a mean value and a dispersion of a strain in the strain-distribution display region 111 using the strain distribution information that is calculated by the strain-distribution calculating unit 123b. The indicator calculating unit 141 calculates a value by dividing the mean value of a strain by the dispersion of a strain as an indicator. The reference-information generating unit 142 according to the second embodiment generates a waveform in which the indicator (mean strain/dispersion) is plotted along the time axis as the reference information. The image memory 15 stores the indicator.

Specifically, the indicator used in the second embodiment is expressed in magnitude of a mean value relative to the dispersion, and the larger the value is, the smaller the variation to the mean value is, to be a value considered that pressure and release are performed appropriately.

FIG. 9A shows an example of the reference information that is displayed in the reference-information display region 130 shown in FIG. 2 at the real-time display. FIG. 9B shows an example of the reference information that is displayed in the reference-information display region 130 at the time when the freeze button is pressed. FIG. 9C shows an example of the reference information that is displayed in the reference-information display region 130 at the time of cine-playing after the freeze button is pressed. 401 shown in FIG. 9A, FIG. 9B, and FIG. 9C signifies a waveform of an indicator "mean strain/dispersion", and 402 signifies the time axis cursor displayed on the monitor 2. The horizontal axis shown in FIG. 9A, FIG. 9B, and FIG. 9C is the time axis indicating time (t) at the time of generation of each frame, and is a time phase at the time of generation of strain information. The scale of the horizontal axis is determined based on a frame rate at which the strain image data is generated and a memory capacity assigned for cine-play in the image memory 15.

When "mean strain/dispersion" takes a positive value in the waveform 401 shown in FIG. 9A, FIG. 9B, and FIG. 9C, it is indicated that a tissue is "pressured", and when "mean strain/dispersion" takes a negative value, it is indicated that a tissue is "released". In the waveform 401, for example, it can be considered that the larger the absolute value of "mean strain/dispersion" is, the more appropriate the strain information is.

In the real-time display mode, the time axis cursor 402 shown in FIG. 9A is arranged at the position indicating the time phase of the latest frame that is currently displayed on the monitor 2. In the real-time display mode, the reference information is updated by the time axis cursor 402.

When the freeze button is pressed, the time axis cursor 402 moves to the frame at the time of transition to the cine-play mode, that is, the right end point in the waveform 401. In the second embodiment, frames are ranked based on indicators similarly to the first embodiment. For example, the controller 17 chooses strain image data of three time phases having the top three largest absolute values of "mean strain/dispersion" as display candidates.

Accordingly, when the freeze button is pressed, three markers (marker 403a, marker 403b, and marker 403c) indicating the ranks and the time phases of the top three "mean strain/dispersion" are displayed in the reference-information display region 130 as shown in FIG. 9B.

The marker 403a is a marker indicating that the absolute value is the first rank, and is formed with a character "1" and a black dot on a waveform as shown in FIG. 9B. Moreover, the marker 403b is a marker indicating that the absolute value is the second rank, and is formed with a character "2" and a black dot on a waveform as shown in FIG. 9B. Furthermore, the marker 403c is a marker indicating that the absolute value is the third rank, and is formed with a character "3" and a black dot on a waveform as shown in FIG. 9B.

In the second embodiment also, strain image data of the frames of top ranks is retrieved from the image memory 15 and displayed on the monitor 2, for example, according to rotation of the trackball by an operator, in the cine-play mode.

When the predetermined order is the rank order, the frames to be displayed according to rotation of the trackball is "the frame corresponding to the position of the marker 403a, the frame corresponding to the position of the marker 403b, and then the frame corresponding to the position of the marker 403c". When the predetermined order is the temporal order, the frames to be displayed according to rotation of the trackball is "the frame corresponding to the position of the marker 403b, the frame corresponding to the position of the marker 403c, and then the frame corresponding to the position of the marker 403*a*". When the direction of rotation is reversed, the order of display is reversed.

In the cine-play mode, the time axis cursor 402 is displayed at a position corresponding to the displaying past time phase on the time axis as shown in FIG. 9C.

The processing performed by the ultrasonic diagnostic apparatus according to the second embodiment is similar to the processing performed by the ultrasonic diagnostic apparatus according to the first embodiment explained using FIG. 8 except that an indicator is, for example, "mean strain/dispersion" in, the explanation thereof is omitted.

As described above, in the second embodiment, it is possible to calculate an indicator with which the state of pressure and release can be determined more objectively, by using a dispersion in addition to a statistical value such as a mean value, a maximum value, and a median value.

In the second embodiment, a case where "mean strain/dispersion" is used as an example of an indicator has been explained. However, in the second embodiment, a statistical value such as a mean value, a maximum value, a median value of a displacement of a tissue and a dispersion of a displacement of a tissue can be used as an indicator. Because a displacement of a tissue is a value that is calculated in the process of calculation of a strain by the strain-distribution calculating unit 123*b*, the indicator calculating unit 141 can calculate, for example, "mean displacement/dispersion" in the strain-distribution display region 111. Moreover, in the second embodiment, a mean value and a dispersion of a strain of a tissue can be used as an indicator. In this case, the indicator calculating unit 141 calculates "mean strain/dispersion" in the strain-distribution display region 111 from the strain distribution information calculated by the strain-distribution calculating unit 123*b*. Furthermore, in the second embodiment, a statistical value such as a mean value, a maximum value, and a median value of a strain ratio and a dispersion of a strain ratio can be used as an indicator. The two regions are, for example, the reference region and the target region. In this case, the indicator calculating unit 141 calculates, for example, "mean strain ratio/dispersion" from data output from the strain-ratio calculating unit 123*c* to output to the reference-information generating unit 142.

Moreover, in the second embodiment, a statistical displacement and a dispersion of a tissue, a statistical velocity and a dispersion, a statistical strain and a dispersion, and a statistical strain ratio and a dispersion can be calculated in multiple combinations, and a candidate time phase can be chosen using these indicators. As described, in the second embodiment, the indicator calculating unit 141 can calculate one of a statistical value and a dispersion of a displacement of a tissue, a statistical value and a dispersion of a velocity of a tissue, a statistical value and a dispersion of a strain of a tissue, a statistical value and a dispersion of a strain ratio of two regions of a tissue, as an indicator.

In the first embodiment and the second embodiment described above, a case where multiple pieces of strain image data chosen based on an indicator are sequentially displayed in a moving image on the monitor 2, for example, according to the operation of the trackball by an operator has been explained. However, the first embodiment and the second embodiment are also applicable to a case where a strain image data group including the strain image data chosen for display is controlled to be displayed in a moving image on the monitor 2 when a display request from an operator is received. Specifically, the controller 17 can control to display the strain image data group including the strain image data of the candidate time phase in a moving image on the monitor 2 when a display request is received from an operator. The strain image data group to be displayed in a moving image corresponds to, for example, multiple pieces of strain image data that are extracted based on indicators. In this case, the order of display in a moving image can be in the rank order or in the temporal order.

Moreover, the strain image data group to be displayed in a moving image can be a strain image data group explained below. For example, an operator specifies one marker by referring to multiple markers indicating ranks and time phases. In this case, the controller 17 controls to display in a moving image, on the monitor 2, a strain image data group that is generated at constant intervals in a predetermined time period (for example, for 5 seconds) having the time phase corresponding to the specified marker in the middle. The length of a moving image in which respective pieces of image data are displayed in a moving image corresponds to, for example, a time interval at which an indicator is calculated. Alternatively, for example, the controller 17 can control to display, in a moving image, a strain image data group that is generated in a predetermined time having the time phase at which each strain image data is generated in the middle, for each of multiple pieces of strain image data chosen based on an indicator. By displaying, together with the strain image data of the candidate time phase, a strain image data group generated before and after the strain image data in a moving image, it is possible to improve possibility of choosing more appropriate strain image data by an operator.

Furthermore, when the moving image display is performed, the controller 17 is not limited to display a marker in a line form as a marker indicating a time phase corresponding to each image data chosen as a candidate as described above. For example, the controller 17 can control to display a marker (for example, a marker in a rectangular form) indicating a time region including a time phase corresponding to each strain image data that is chosen as a candidate, instead of a marker in a line form.

Moreover, in the first embodiment and the second embodiment described above, a case where multiple candidate time phases are extracted has been explained. However, the first embodiment and the second embodiment are applicable to a case where a single candidate is extracted. For the candidate, for example, the first rank time phase or the time phase that is closest to the time of depression of the freeze button is chosen among top three candidate time phases. Furthermore, in the first embodiment and the second embodiment described above, a case where the extraction processing of a candidate time phase and the ranking processing are performed, triggered by reception of a direction by an operator has been explained. However, the first embodiment and the second embodiment are applicable to a case where the extraction processing of a candidate time phase and the ranking processing are performed in parallel to newly generating strain information and strain image data.

Moreover, an indicator used in the first embodiment and the second embodiment described above can be an indicator other than the one described above. For example, a case where one of a velocity, a dispersion, and a power of Doppler information included in tissue Doppler data, or a combination thereof is used as an indicator is also applicable. Furthermore, for example, a case where a signal-to-noise (S/N) ratio of a reception signal is used in addition thereto as an indicator is also applicable. Moreover, for example, a case where a waveform of a local section that includes the indicator at which an appropriate strain distribution has been acquired in a past examination is recorded as a training data, and a section that has a high similarity to the waveform of the training data is chosen as a candidate time phase is also applicable.

Furthermore, in the first embodiment and the second embodiment described above, the controller 17 can rank and extract multiple candidate time phases based on an indicator associated with each time phase and information acquired from the B-mode image data that is generated at the time phase. The information acquired from the B-mode image data is, for example, a signal-to-noise ratio. In this case, the controller 17 can rank and extract multiple candidate time phases using a value acquired by multiplying an absolute value of a mean moving velocity of a region of interest in a time phase by a coefficient that is determined by an S/N ratio in the region of interest of the B-mode image data of the time phase. For example, for a time phase for which an excellent S/N ratio (S/N ratio of high value) is obtained, it can be determined that an image with low noise and high reliability is obtained, and therefore, a high coefficient value is set. Such processing to set a coefficient is executed, for example, by setting a function to calculate a coefficient from a value of an S/N ratio, or a table in which a value of an S/N ratio is associated with a coefficient, in the controller 17 in advance.

Alternatively, the controller 17 can rank and extract multiple candidate time phases based on an indicator associated with each time phase and information acquired from the tissue-Doppler image data that is generated at the time phase. The information acquired from the tissue-Doppler image data is, for example, a signal-to-noise ratio. The controller 17 uses a dispersion value of a tissue at each sample point generated as the tissue-Doppler data. The dispersion value of the tissue Doppler data can be used as a value corresponding to the S/N ratio in the B-mode image data. Therefore, the controller 17 can rank and extract multiple candidate time phases using a value acquired by multiplying an absolute value of a mean moving velocity of a region of interest in a time phase by a coefficient that is determined by a value (dispersion value) of a region of interest in the tissue-Doppler image data (dispersion image data) of the time phase. For example, for a time phase for which a large dispersion value is obtained, it can be determined that variations among Doppler signals are large and an image with low reliability is obtained, and therefore, a low coefficient value is set. Such coefficient setting processing can be executed by setting, for example, a function to calculate a coefficient from a dispersion value, or a table in which a dispersion value and a coefficient are associated, in the controller 17 in advance.

A value of information that is obtained from the B-mode image data, the tissue-Doppler image data, and the like is not limited to the value described above. For example, the controller 17 can rank and extract multiple candidate time phases using an indicator and a power value of the tissue-Doppler image data (power image data). In this case, the controller 17 performs ranking in which a time phase having a large power value takes higher priority. For example, the controller 17 sets a high coefficient value to a time phase for which a large power value is obtained. Furthermore, the controller 17 can rank and extract multiple candidate time phases using an indicator and a mean brightness value of the B-mode image data. In this case, the controller 17 performs ranking in which a time phase having a large mean brightness value takes higher priority. For example, the controller 17 sets a high coefficient value to a time phase for which a large mean brightness value is obtained.

As described, by further using a value of information that is obtained from other image data generated in the same time phase as the strain image data, the controller 17 can avoid extraction of a time phase the S/N ratio of which is poor although it is calculated by a value having a large absolute value of the mean moving velocity as a candidate phase, for example. In other words, the controller 17 can avoid a time phase with low reliability to be extracted by ranking each time phase using a value of information acquired from image data (the B-mode image data, the tissue-Doppler image data, and the like) together with an indicator.

To avoid extraction of a candidate time phase with low reliability, the controller 17 can perform following processing. Specifically, the controller 17 excludes a time phase for which a value of information that is acquired from the other image data generated in the same time phase as the strain image data does not meet predetermined conditions. For example, the controller 17 excludes a time phase the S/N ratio of which is below a preset threshold, or a time phase a dispersion value of which exceeds a preset threshold. The controller 17 then ranks and extracts the candidate time phases using indicators associated with the rest of respective time phases. Accordingly, the controller 17 can avoid extraction of a time phase the S/N ratio of which is poor although it is calculated by a value having a large absolute value of the mean moving velocity as a candidate phase, for example.

Alternatively, the controller 17 can set, for the time phase for which a value of information acquired from the other image data that is generated in the same time phase as the strain image data does not satisfy predetermined conditions, the coefficient value by which an indicator of the time phase is multiplied to "0", as processing equivalent to the exclusion processing described above. In this case, for example, the controller 17 sets the coefficient value by which an indicator of the time phase is multiplied to "0" for a time phase the S/N ratio of which is below a preset threshold, or a time phase a dispersion value of which exceeds a preset threshold, and ranks and extracts candidate time phases.

Furthermore, as a modification of the above example, the controller 17 can rank and extract multiple candidate time phases based on an indicator associated with each time phase, a value of information acquired from the B-mode image data generated in the same time phase, and a value of information acquired from the tissue-Doppler image data that is generated in the time phase.

Furthermore, the image processing method explained in the first embodiment and the second embodiment can be performed by an image processing apparatus that can acquire reflection wave data from a database that stores medical image data.

Moreover, the respective components in the respective apparatuses shown in the explanation of the first embodiment and the second embodiment are functional concept, and it is not necessarily required to be physically configured as shown in the drawings. Specifically, a specific form of distribution and integration of the respective apparatuses are not limited to the ones shown in the drawings, and it can be configured such that all or a part thereof are functionally or physically distributed or integrated in arbitrary units according to various kinds of load and usage condition. For example, the tissue-information processing unit 123 can be integrated with the blood-flow-information processing unit 122. Furthermore, for example, the strain-ratio calculating unit 123c can be arranged in the strain-information processing unit 14. Further, as for the respective processing functions of the respective apparatuses, all or an arbitrary part thereof can be implemented by a central processing unit (CPU) and a computer program that is analyzed and executed by the CPU, or can be implemented as hardware by wired logic.

Moreover, the image processing method explained in the first embodiment and the second embodiment can be implemented by executing an image processing program prepared in advance by a computer such as a personal computer and a work station. The image processing program can be distributed through the Internet or a network. Furthermore, the image processing program can be stored in a computer-readable non-temporary recording medium such as a hard disk, a flexible disk (FD), a compact-disc read-only memory (CD-ROM), a magneto optical disk (MO), a digital versatile disc (DVD), and a flash memory including a universal serial bus (USB) memory and a secure digital (SD) card and the like, and can be executed by being read by a computer from the non-temporary recording medium.

As described above, according to the first embodiment and the second embodiment, it is possible for an operator to acquire appropriate information about a strain easily.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An ultrasonic diagnostic apparatus comprising:
a processor configured to
generate, based on a reflection wave signal of an ultrasonic wave that is transmitted into a subject, strain information indicating a spatial distribution of a strain of a tissue that is pressured and released in the subject for each of a plurality of time phases;
calculate an indicator indicating pressure and release to the tissue at generation of the strain information, based on the reflection wave signal;
control to store a plurality of images in a memory, each of the plurality of images being generated based on the spatial distribution indicated by the strain information and corresponding to each of the plurality of time phases;
rank the plurality of time phases based on magnitude of the indicator;
extract first time phases among the plurality of time phases, based on the ranking of the plurality of time phases; and
control to display, in a display order, at least two of the plurality of images stored in the memory corresponding to the extracted first time phases,
wherein the display order of the at least two images is based on a result of the ranking of the plurality of time phases such that an image corresponding to a second rank in the ranking is displayed immediately after an image corresponding to a first rank in the ranking is displayed.

2. The ultrasonic diagnostic apparatus according to claim 1, wherein the processor further controls to display, on the display, at least one of information about the extracted first time phases and a value about the strain information for the extracted first time phases.

3. The ultrasonic diagnostic apparatus according to claim 1, wherein the processor further generates the indicator indicating the pressure and release as a reference information in a form of a chronological waveform, and controls to display information indicating the extracted first time phases in the reference information when a display request of an image data group stored in the memory is received from an operator.

4. The ultrasonic diagnostic apparatus according to claim 3, wherein the processor controls to further display information about a rank of the extracted first time phases in the reference information.

5. The ultrasonic diagnostic apparatus according to claim 1, wherein the processor generates a strain ratio that is calculated from a ratio of strain distributions in predetermined two regions on a space as the strain information.

6. The ultrasonic diagnostic apparatus according to claim 1, wherein the processor calculates at least one of a statistical value of a displacement of the tissue, a statistical value of a velocity of the tissue, a statistical value of the strain of the tissue, and a statistical value of a strain ratio of two regions in the tissue, as the indicator.

7. The ultrasonic diagnostic apparatus according to claim 1, wherein the processor calculates at least one of a statistical value and a dispersion of a displacement of the tissue, a statistical value and a dispersion of a velocity of the tissue, a statistical value and a dispersion of a strain of the tissue, and a statistical value and a dispersion of a strain ratio of two regions in the tissue, as the indicator.

8. The ultrasonic diagnostic apparatus according to claim 1, wherein the processor
performs the calculation of the indicator at predetermined time intervals, and
controls to store the calculated indicator in the memory, wherein
the predetermined time intervals are associating with image data based on the strain information generated at the time of the calculation of the indicator.

9. The ultrasonic diagnostic apparatus according to claim 1, wherein the processor controls to perform cine-playing or video playing the plurality of images on a display based on the result of the ranking.

10. The ultrasonic diagnostic apparatus according to claim 1, wherein the processor controls to store, in the memory, second time phases in association with image data and the indicator, the second time phases being time phases at the generation of the strain information, the image data being generated based on the strain information and the indicator being an indicator at the generation of the strain information.

11. The ultrasonic diagnostic apparatus according to claim 1, wherein the processor controls to store, in the memory, second time phases in association with image data and the indicator, the second time phases being time phases at the generation of the strain information, the image data being generated based on the strain information and the indicator being an indicator at the generation of the strain information; and extract the first time phases based on the indicator associated with each of the second time phases.

12. The ultrasonic diagnostic apparatus according to claim 11, wherein the processor ranks and extracts the first time phases based on the indicator associated with each of the second time phases, or ranks and extracts the first time phases based on the indicator associated with each of the second time phases, any one of B-mode image data that is generated at each of the second time phases, and information that is acquired from tissue-Doppler image data.

13. The ultrasonic diagnostic apparatus according to claim 1, wherein the processor calculates, as the indicator, a value comparing a mean value of the strain of the tissue to a value obtained from the strain of the tissue that is different from the mean value.

14. An image processing method comprising:
generating, based on a reflection wave signal of an ultrasonic wave that is transmitted into a subject, a strain information indicating a spatial distribution of a strain of a tissue that is pressured and released in the subject in chronological order by a processor;
calculating by the processor, an indicator indicating of pressure and release to the tissue at generation of the strain information, based on the reflection wave signal;
controlling by the processor, to store a plurality of images in a memory, each of the plurality of images being generated based on the spatial distribution indicated by the strain information and corresponding to each of the plurality of time phases;
ranking, by the processor, the plurality of time phases, based on magnitude of the indicator;
extracting by the processor, time phases among the plurality of time phases, based on the ranking of the plurality of time phases; and
controlling by the processor, to display, in a display order, at least two images of the plurality of images stored in the memory,
wherein the display order of the at least two images is based on a result of the ranking of the plurality of time phases such that an image corresponding to a second rank in the ranking is displayed immediately after an image corresponding to a first rank in the ranking is displayed.

15. An ultrasonic diagnostic apparatus comprising:
a processor configured to
generate, based on a reflection wave signal of an ultrasonic wave that is transmitted into a subject, strain information indicating a spatial distribution of a strain of a tissue that is pressured and released in the subject for each of a plurality of time phases;
calculate an indicator indicating pressure and release to the tissue at generation of the strain information, based on the reflection wave signal; control to store a plurality of images in a memory, each of the plurality of images being generated based on the spatial distribution indicated by the strain information and corresponding to each of the plurality of time phases;
rank the plurality of images based on magnitude of the indicator;
extract at least two images among the plurality of images based on the ranking of the plurality of images; and
control to display, in a display order, at least two of the plurality of images stored in the memory corresponding to the extracted first time phases,
wherein the display order of the at least two images is based on a result of the ranking of the plurality of time phases such that an image corresponding to a second rank in the ranking is displayed immediately after an image corresponding to a first rank in the ranking is displayed.

16. The ultrasonic diagnostic apparatus according to claim 1, wherein the processor calculates, as the indicator, a value comparing a mean value of the strain of the tissue to a value obtained from the strain of the tissue that is different from the mean value.

* * * * *